United States Patent
Hwang et al.

(10) Patent No.: US 11,880,003 B2
(45) Date of Patent: Jan. 23, 2024

(54) APPARATUS AND METHOD FOR MEASURING DISTRIBUTION OF RADIATION DOSE FROM BRACHYTHERAPY RADIATION SOURCE

(71) Applicants: THE INDUSTRY & ACADEMIC COOPERATION IN CHUNGNAM NATIONAL UNIVERSITY (IAC), Daejeon (KR); CHUNGNAM NATIONAL UNIVERSITY HOSPITAL, Daejeon (KR); NATIONAL CANCER CENTER, Goyang-si (KR); KOREA INSTITUTE OF RADIOLOGICAL & MEDICAL SCIENCES, Seoul (KR)

(72) Inventors: Ui-Jung Hwang, Goyang-si (KR); Young Kyung Lim, Paju-si (KR); Sang Hyoun Choi, Namyangju-si (KR); Youngmoon Goh, Goyang-si (KR); Ki Hwan Kim, Daejeon (KR)

(73) Assignees: THE INDUSTRY & ACADEMIC COOPERATION IN CHUNGNAM NATIONAL UNIVERSITY (IAC), Daejeon (KR); CHUNGNAM NATIONAL UNIVERSITY HOSPITAL, Daejeon (KR); NATIONAL CANCER CENTER, Goyang-si (KR); KOREA INSTITUTE OF RADIOLOGICAL & MEDICAL SCIENCES, Seoul (KR)

(*) Notice: Subject to any disclaimer, the term of this patent is extended or adjusted under 35 U.S.C. 154(b) by 130 days.

(21) Appl. No.: 17/438,938

(22) PCT Filed: Mar. 12, 2020

(86) PCT No.: PCT/KR2020/003486
§ 371 (c)(1),
(2) Date: Sep. 14, 2021

(87) PCT Pub. No.: WO2020/185024
PCT Pub. Date: Sep. 17, 2020

(65) Prior Publication Data
US 2022/0155466 A1 May 19, 2022

(30) Foreign Application Priority Data
Mar. 14, 2019 (KR) .................. 10-2019-0029239

(51) Int. Cl.
*G01T 1/10* (2006.01)
*A61N 5/10* (2006.01)
(Continued)

(52) U.S. Cl.
CPC .............. *G01T 1/10* (2013.01); *A61N 5/1001* (2013.01); *A61N 5/1007* (2013.01); *G01T 1/161* (2013.01); *G01T 1/2914* (2013.01); *G01T 7/00* (2013.01)

(58) Field of Classification Search
CPC ......... G01T 1/10; G01T 1/161; G01T 1/2914; G01T 7/00; A61N 5/1001; A61N 5/1007
See application file for complete search history.

(56) References Cited

U.S. PATENT DOCUMENTS

| | | | | |
|---|---|---|---|---|
| 5,635,709 A | * | 6/1997 | Sliski | G01T 1/169 378/207 |
| 2012/0168630 A1 | * | 7/2012 | Beddar | G01T 1/204 250/362 |
| 2015/0306427 A1 | * | 10/2015 | Hirasawa | G01T 1/204 250/363.08 |

FOREIGN PATENT DOCUMENTS

| | | |
|---|---|---|
| JP | 2008049145 | 3/2008 |
| JP | 2017187286 | 10/2017 |

(Continued)

*Primary Examiner* — Christine S. Kim

(74) *Attorney, Agent, or Firm* — LEX IP MEISTER, PLLC

(57) ABSTRACT

Disclosed is an apparatus for measuring the distribution of radiation dose emitted from a brachytherapy insertion tool, the apparatus including a housing having defined therein a measurement space in which the brachytherapy insertion tool is located, a fluorescent member disposed at the housing, the fluorescent member being configured to react with radiation emitted to the measurement space and to emit light, a camera disposed in the housing, and a cover coupled to one surface of the housing, the cover being configured to cover the fluorescent member. The portion of the fluorescent member to which radiation from a radiation source of the brachytherapy insertion tool is applied reacts with the radiation and generates light, brightness of the light varies depending on distribution of the radiation, and the position at which the light is bright is calculated to measure the direction in which the brachytherapy insertion tool has no shielding.

8 Claims, 10 Drawing Sheets

(51) Int. Cl.
*G01T 1/161* (2006.01)
*G01T 1/29* (2006.01)
*G01T 7/00* (2006.01)

(56) References Cited

FOREIGN PATENT DOCUMENTS

| KR | 20140137731 | | 12/2014 |
|---|---|---|---|
| KR | 20150116223 | | 10/2015 |
| KR | 20170074559 | A * | 6/2017 |

\* cited by examiner

[FIG. 1]
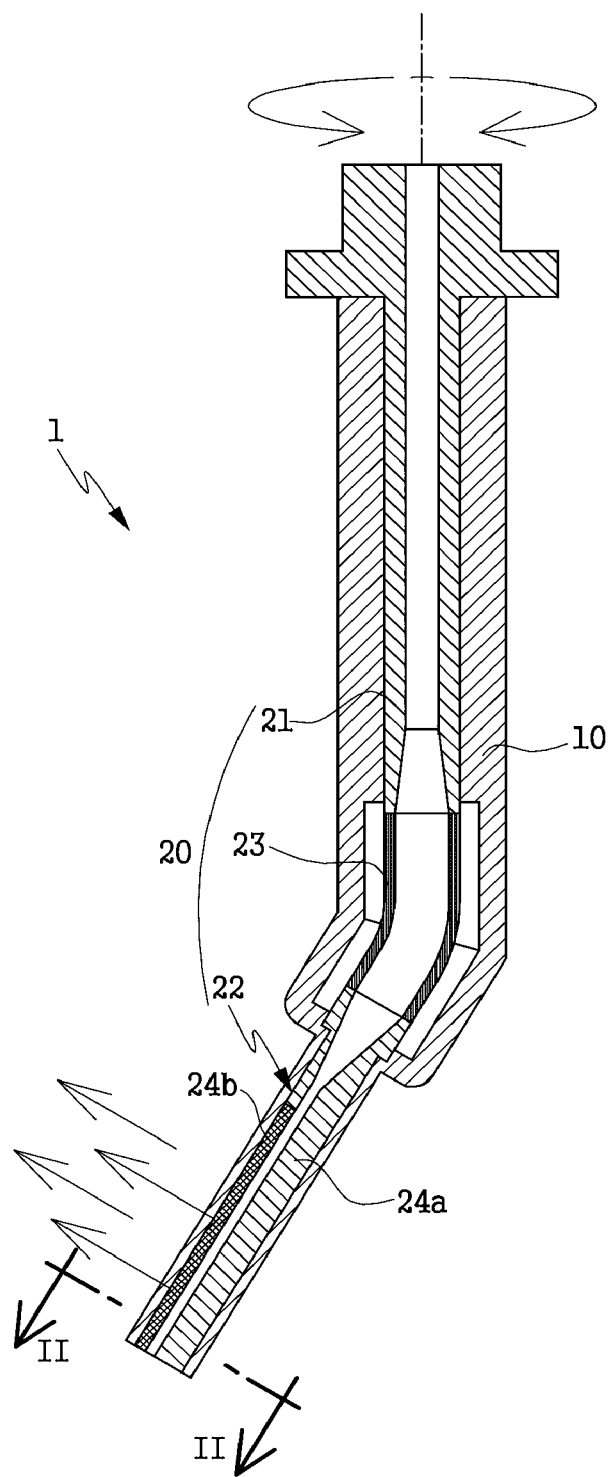

[FIG. 2]
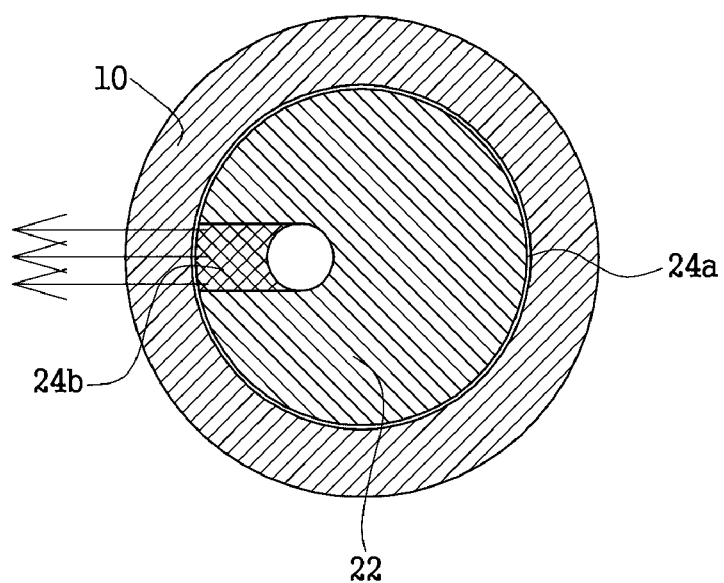

[FIG. 3]
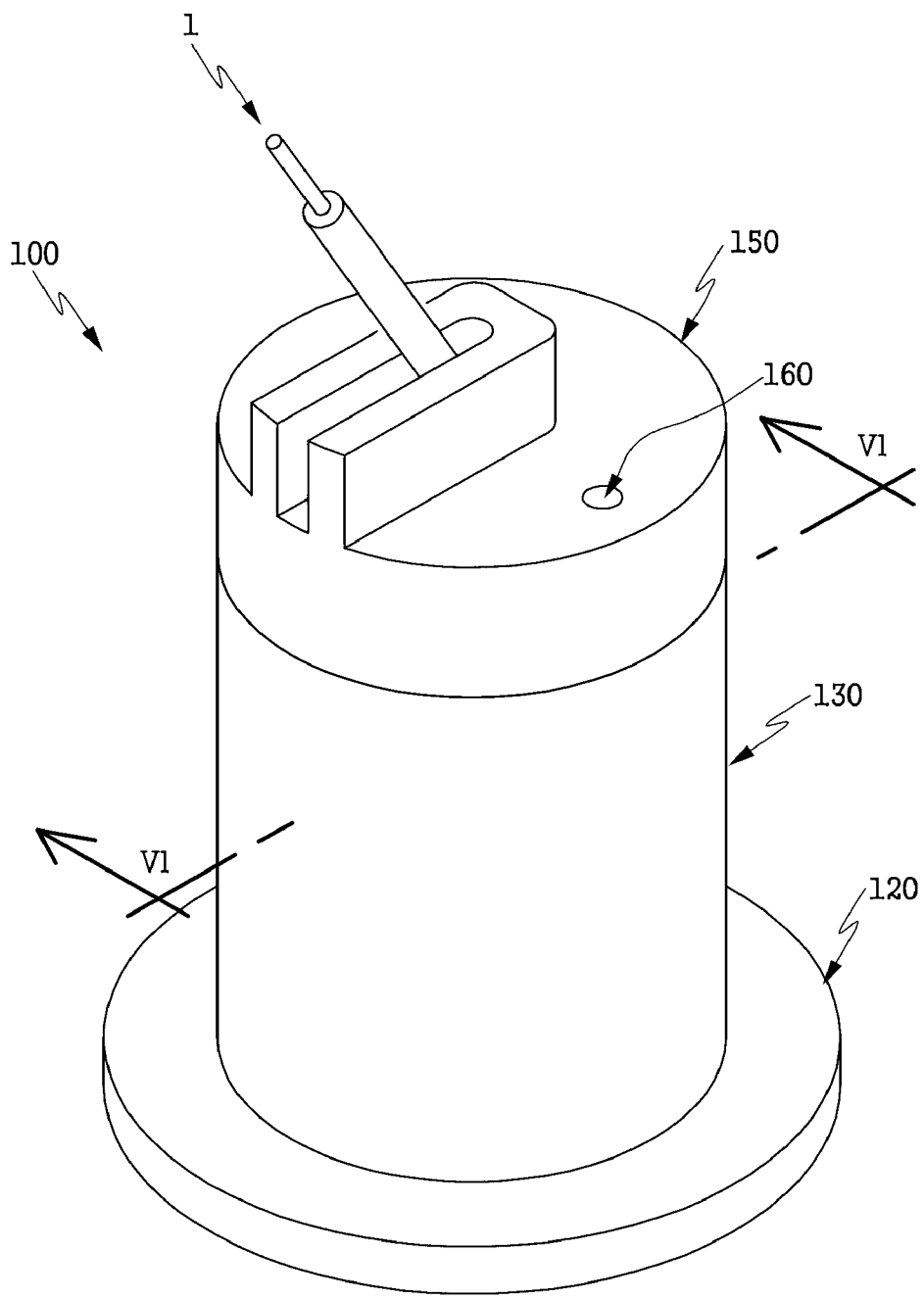

[FIG. 4]
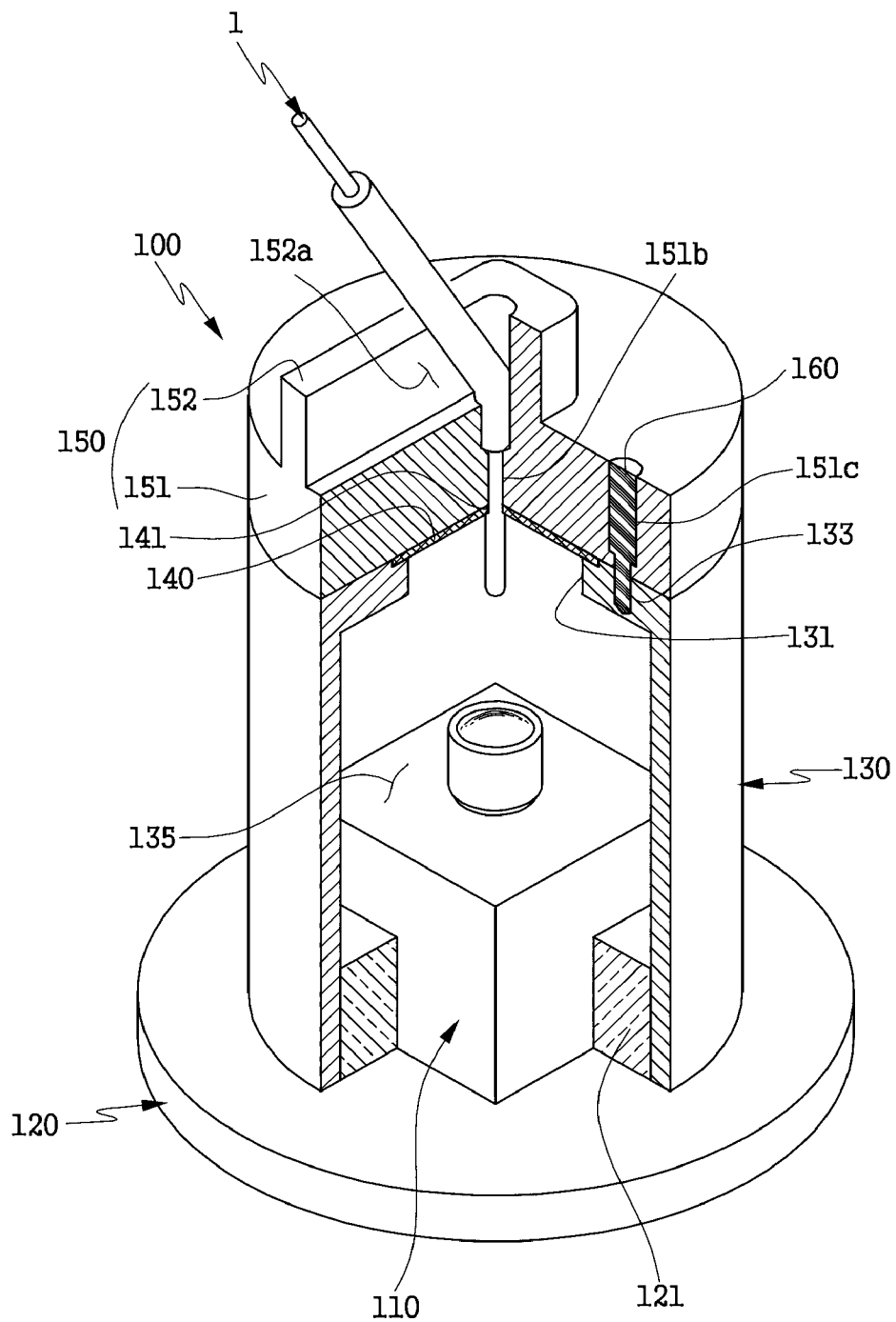

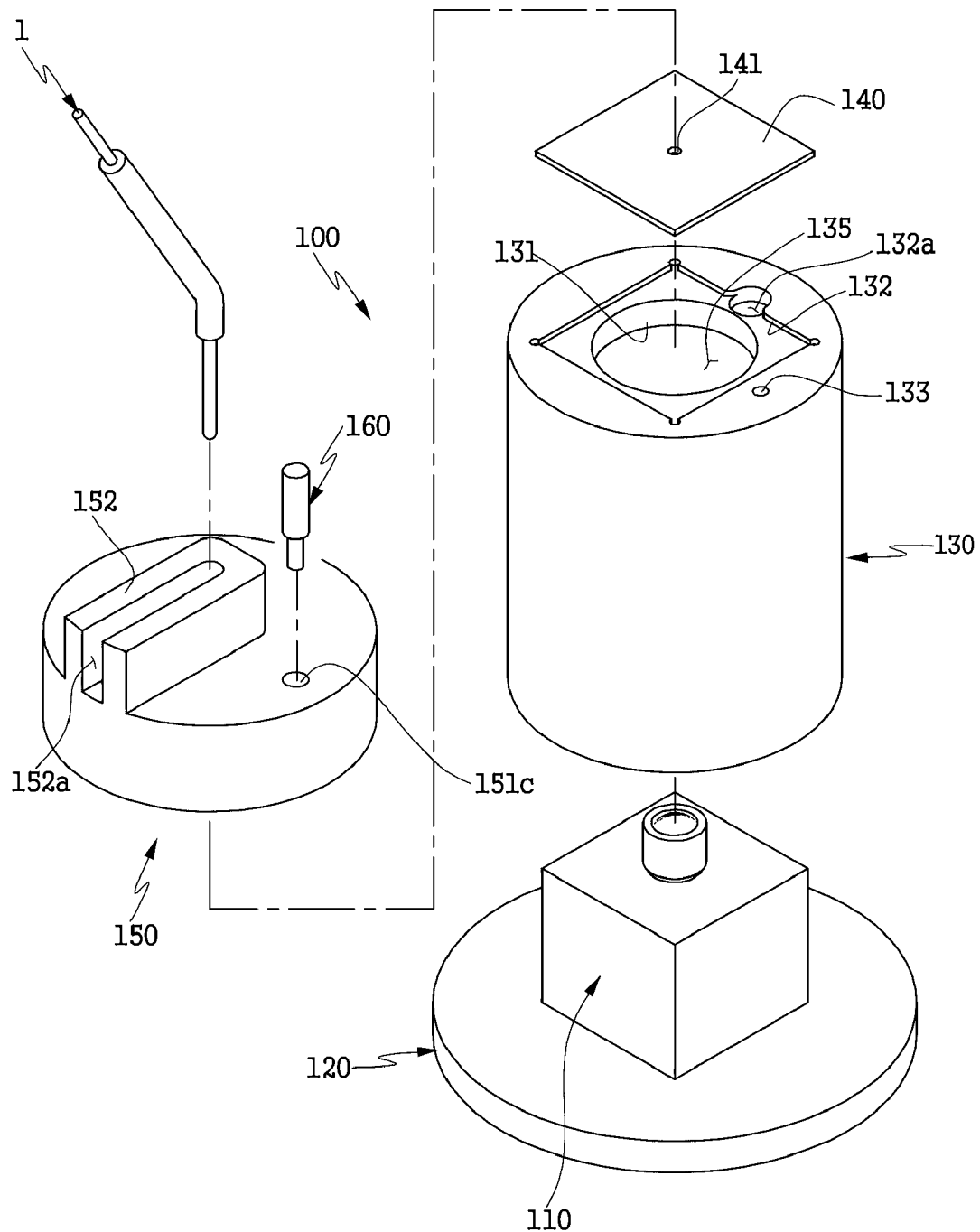
[FIG. 5]

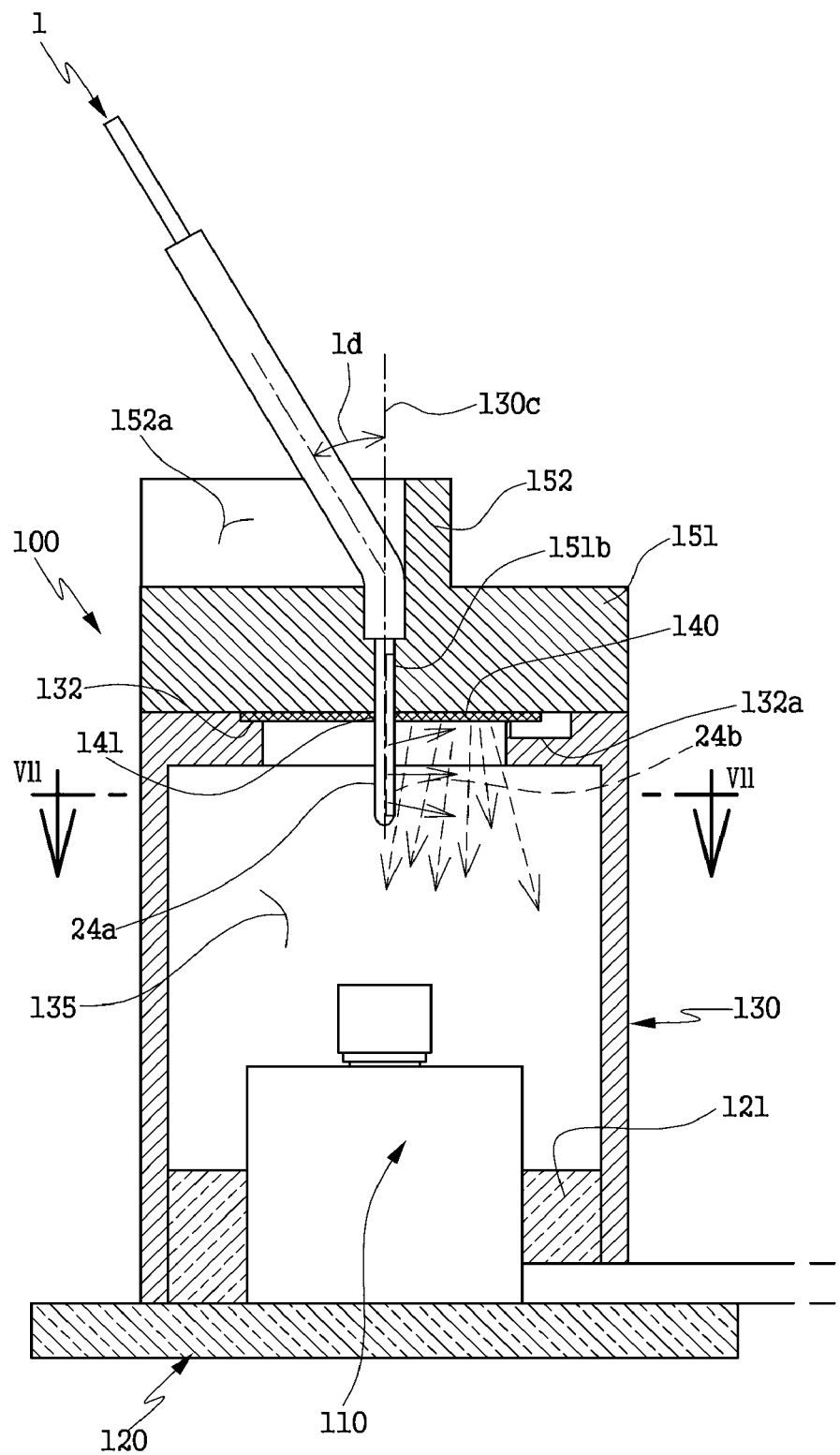
[FIG. 6]

[FIG. 7]
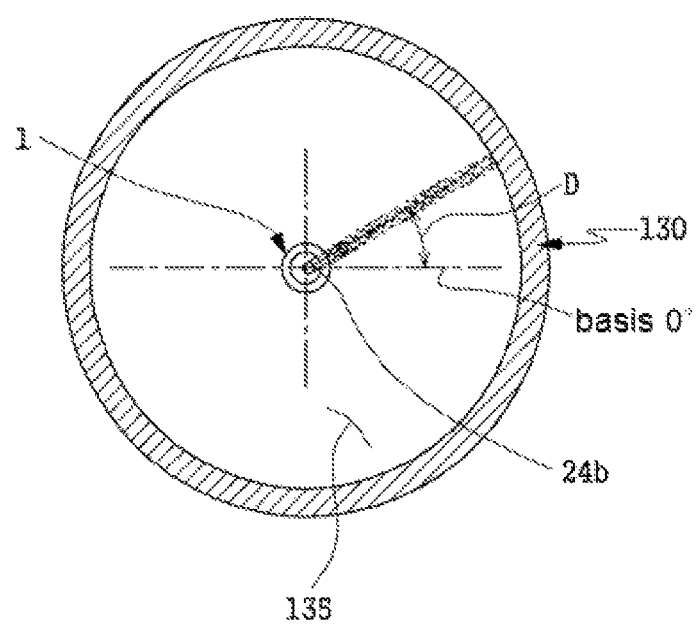

[FIG. 8]
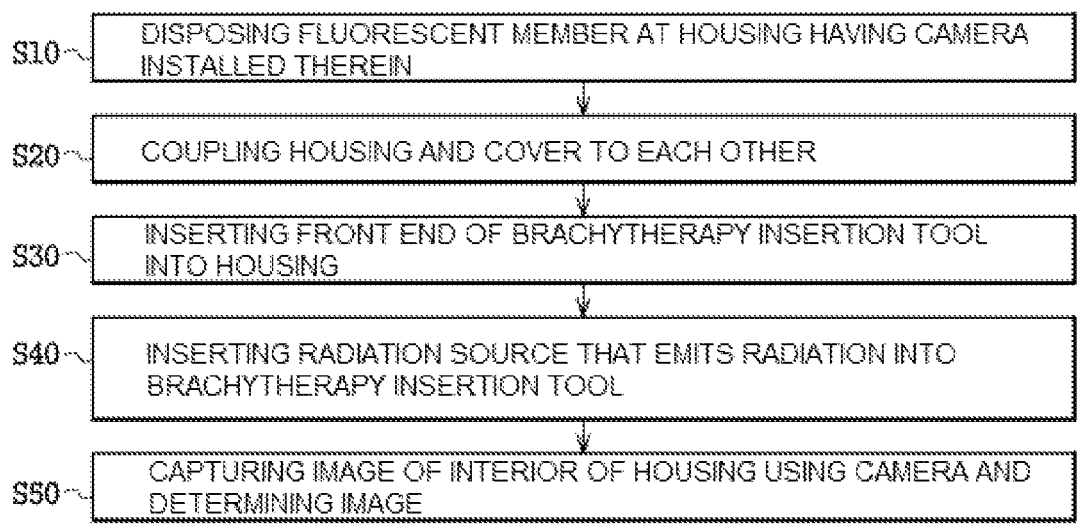

[FIG. 9]
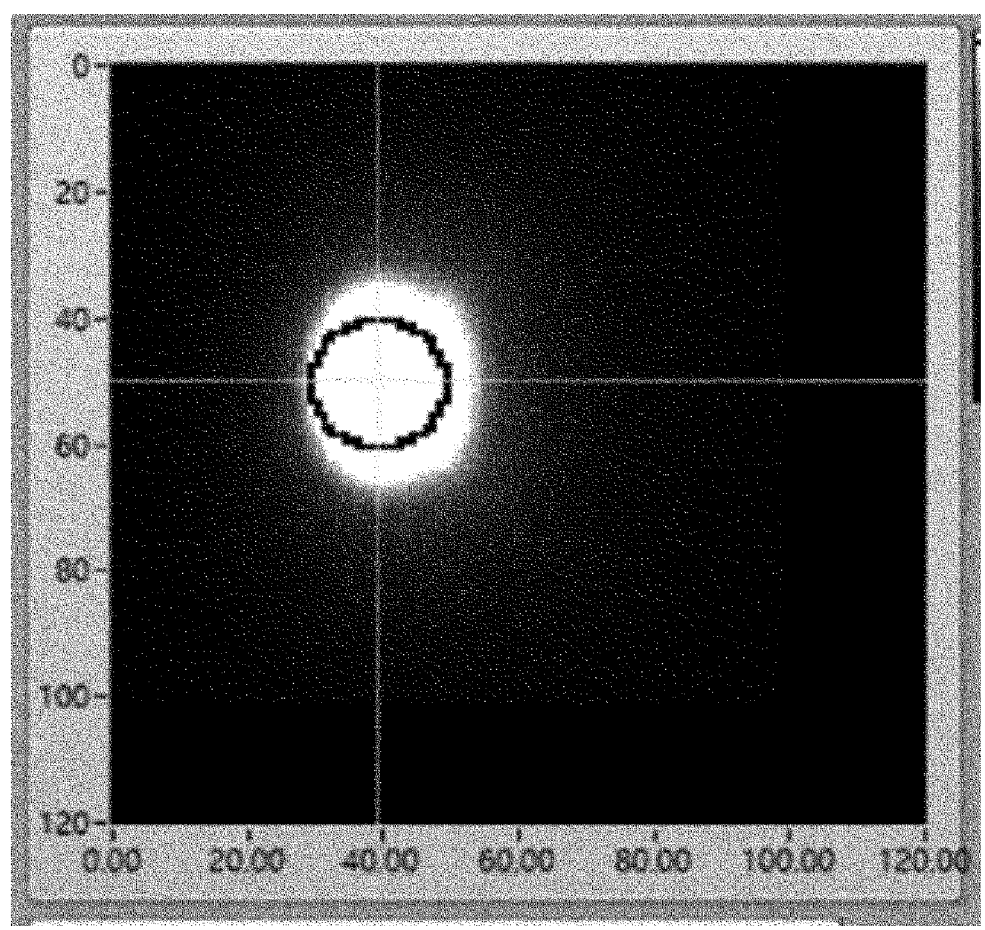

[FIG. 10]
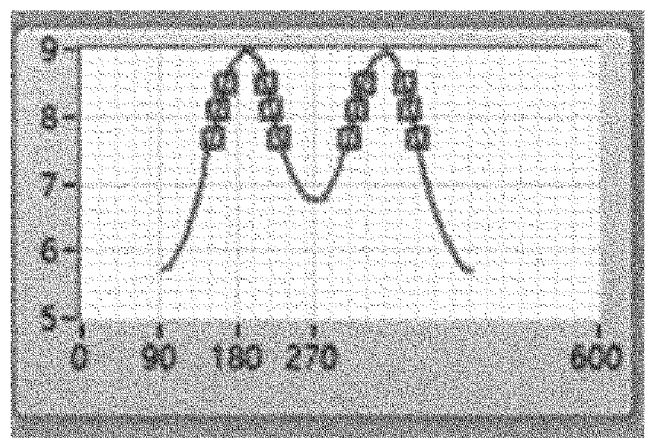

APPARATUS AND METHOD FOR MEASURING DISTRIBUTION OF RADIATION DOSE FROM BRACHYTHERAPY RADIATION SOURCE

TECHNICAL FIELD

The present invention relates to an apparatus and method for measuring the distribution of radiation dose from a brachytherapy radiation source.

BACKGROUND ART

Radiation therapy is a clinical medicine method that treats patients using radiation having a very short wavelength and high energy, and is one of three major cancer treatments together with surgery and chemotherapy. Although radiation therapy treats malignant tumors mainly called cancer, radiation therapy also treats benign tumors or some benign diseases.

Radiation therapy may be classified as teletherapy and brachytherapy depending on the position of a radiation applicator.

Teletherapy is a treatment method that applies radiation using various kinds of equipment outside the human body, and may be classified as photon beam therapy, electron beam therapy, or particle therapy (neutron therapy, proton therapy, etc.) depending on the kind of radiation that is used. Although various radiation generators may be used, therefore, a radiation generator that is the most widely used is a linear accelerator.

Brachytherapy is a method of locating a radiation generator or a radiation source in the human body or at the surface of the human body to apply radiation to a limited region, and may be classified as intracavitary radiotherapy, intraluminal radiotherapy, interstitial radiotherapy, or contact therapy depending on the space into which the radiation generator or the radiation source is inserted or a method in which the radiation generator or the radiation source is inserted.

As shown in FIGS. 1 and 2, a brachytherapy insertion tool 1, which is configured to be inserted into a human body, includes an outer body 10 and an inner body 20 located in the outer body 10. Here, the middle portion of the outer body 10 in a longitudinal direction thereof is bent at a predetermined angle such that the front part of the brachytherapy insertion tool 1 can be easily inserted into the human body. The inner body 20 is divided into a first portion 21 and a second portion 22, and the first portion 21 and the second portion 22 are connected to each other via a flexible connection portion 23. The connection portion 23 is located at the bent portion of the outer body 10. When the first portion 21 is rotated, rotational force is transmitted to the second portion 22 via the connection portion 23, whereby the second portion 22 is rotated.

Interiors of the first portion 21, the connection portion 23, and the second portion 22 are connected to each other, and a radiation source (not shown) may be located in the second portion 22 via the first portion 21 and the connection portion 23.

The second portion 22 is inserted into the human body so as to be located at a place adjacent to a tumor. Here, the second portion 22 may be divided into a first region 24a and a second region 24b. The first region 24a has radiation shielding, and the second region 24b has no radiation shielding. As a result, a larger amount of radiation is emitted from the second region 24b than the first region 24a.

Consequently, control is performed such that the first region 24a faces a normal site and the second region 24b faces a tumor site in the state in which the second portion 22 is inserted into the human body. Radiation generated from the radiation source may be emitted through the second region 24b and the portion of the outer body 10 that faces the second region 24b so as to concentrate on the tumor.

Consequently, the direction of the second region 24b must be adjusted such that the second region faces the tumor in the state in which the brachytherapy insertion tool 1 is inserted into the human body. When the first portion 21 is rotated, the second portion 22 is rotated together with the first portion 21 through the connection portion 23. The position of the second region 24b is also changed as a result of rotation of the second portion 22.

In the case in which rotational force of the first portion 21 is not accurately transmitted to the second portion 22 via the flexible connection portion 23, however, a rotational range of the first portion 21 and a rotational range of the second portion 22 become different from each other, whereby an error is generated. If the second portion 22 does not face the tumor site but faces the normal site due to the error, radiation is applied to the normal site.

Since the second portion 22 is located in the outer body 10, it is not possible to directly check by eye whether an error is generated. Therefore, measurement as to whether the second portion 22, in which the radiation source is located, is accurately rotated together with the first portion 21 and thus the second region 24b faces a predetermined position (a tumor site) is essentially required.

DISCLOSURE

Technical Problem

The present invention provides technology capable of measuring whether radiation from a radiation source of a brachytherapy insertion tool is accurately applied to a predetermined position.

Technical Solution

An apparatus for measuring the distribution of radiation dose emitted from a brachytherapy insertion tool according to an embodiment of the present invention includes a housing having defined therein a measurement space in which the brachytherapy insertion tool is located, a fluorescent member disposed at the housing, the fluorescent member being configured to react with radiation emitted to the measurement space and to emit light, a camera disposed in the housing, and a cover coupled to one surface of the housing, the cover being configured to cover the fluorescent member.

Radiation emitted from a brachytherapy radiation source transferred to the brachytherapy insertion tool may be applied to the fluorescent member in the measurement space to emit light, and an image of the light may be captured by the camera.

The cover may include a cover body having a cover through-hole, through which the brachytherapy insertion tool is inserted, formed therein.

The cover may further include an insertion tool guide formed at the cover body, the insertion tool guide being provided with a guide recess configured to guide the brachytherapy insertion tool to the cover through-hole.

The cover may further include a coupling pin inserted into the housing through the cover, the coupling pin being configured to prevent movement of the cover.

The housing may block external light so as not to be introduced into the measurement space when the brachytherapy insertion tool is mounted to the cover.

The fluorescent member may be flat, may be disposed perpendicular to the brachytherapy insertion tool guided to the measurement space, and may be provided with a fluorescent through-hole, through which the brachytherapy insertion tool is inserted so as to be installed.

The camera may be disposed at one side of the measurement space, and the center of a lens of the camera is located on the same line as the center of the brachytherapy insertion tool inserted into the measurement space.

The apparatus may further include a lifting unit disposed at the housing, the lifting unit being configured to set the position of the fluorescent member.

A method of measuring the distribution of radiation dose from a brachytherapy radiation source according to an embodiment of the present invention includes disposing a fluorescent member at a housing having a camera disposed therein, coupling the housing and a cover to each other in the state in which the fluorescent member is interposed therebetween, inserting the front end of a brachytherapy insertion tool into a measurement space of the housing, transferring a brachytherapy radiation source into the brachytherapy insertion tool, and capturing an image of the measurement space to which radiation is applied and analyzing the captured image.

The portion of the fluorescent member to which radiation from the brachytherapy radiation source is applied may react with the radiation and may generate light, brightness of the light may vary depending on distribution of the radiation, and the position at which the light is bright may be calculated to measure the direction in which the brachytherapy insertion tool has no shielding.

Advantageous Effects

According to an embodiment of the present invention, a fluorescent member reacts with radiation applied to a measurement space and emits light. An image of the emitted light may be captured by a camera, and the captured image may be analyzed to measure the angle of radiation dose. Consequently, it is possible to accurately measure the angle of radiation dose from a brachytherapy insertion tool, whereby it is possible to improve reliability of brachytherapy.

According to the embodiment of the present invention, it is possible to accurately apply radiation to a tumor site through measurement of the angle of radiation dose, whereby it is possible to improve the effect of radiation therapy.

According to the embodiment of the present invention, the front end of the brachytherapy insertion tool is inserted perpendicularly through the fluorescent member, and radiation is applied under the fluorescent member in a direction parallel to the fluorescent member. Since the radiation is emitted in a direction parallel to the fluorescent member, it is possible to more accurately measure the angle of radiation dose from the brachytherapy insertion tool.

According to the embodiment of the present invention, the position of the fluorescent member is changed by a lifting unit, whereby three-dimensional radiation dose distribution measurement is possible. As a result, it is possible to more accurately measure the direction in which a second region faces.

DESCRIPTION OF DRAWINGS

FIG. 1 is a schematic view showing a brachytherapy insertion tool.

FIG. 2 is a sectional view taken along line II-II of FIG. 1.

FIG. 3 is a perspective view showing an apparatus for measuring the distribution of radiation dose from a brachytherapy insertion tool according to an embodiment of the present invention.

FIG. 4 is a sectional perspective view showing the interior of FIG. 3.

FIG. 5 is an exploded perspective view of FIG. 3.

FIG. 6 is a sectional view taken along line VI-VI of FIG. 3.

FIG. 7 is a sectional view taken along line VII-VII of FIG. 6.

FIG. 8 is a block diagram schematically showing a radiation dose distribution measurement method.

FIG. 9 is an image capturing a measurement space to which radiation is applied.

FIG. 10 is a graph showing radiation detection using a contour line.

BEST MODE

Now, embodiments of the present invention will be described in detail with reference to the accompanying drawings such that the embodiments of the present invention can be easily implemented by a person having ordinary skill in the art to which the present invention pertains. However, the present invention may be implemented in various different forms and is not limited to the embodiments described herein. Throughout the specification, similar elements are denoted by the same reference symbols.

Hereinafter, a brachytherapy insertion tool according to an embodiment of the present invention will be described with reference to FIGS. 3 to 7.

FIG. 3 is a perspective view showing an apparatus for measuring the distribution of radiation dose from a brachytherapy insertion tool according to an embodiment of the present invention, FIG. 4 is a sectional perspective view showing the interior of FIG. 3, FIG. 5 is an exploded perspective view of FIG. 3, FIG. 6 is a sectional view taken along line VI-VI of FIG. 3, and FIG. 7 is a sectional view taken along line VII-VII of FIG. 6.

Referring to FIGS. 3 to 7, the apparatus 100 for measuring the distribution of radiation dose from the brachytherapy insertion tool according to the present embodiment includes a housing 130, a fluorescent member 140, and a cover 150, and measures whether radiation applied from a radiation source of the brachytherapy insertion tool is accurately applied to a predetermined position. That is, the radiation dose distribution measurement apparatus measures quality of the brachytherapy insertion tool.

The housing 130 is disposed on a base 120 having a predetermined area, and the interior of the housing is vertically bored such that a measurement space 135 is defined in the housing. The housing 130 is provided in the upper surface thereof with an opening hole 131, which is connected to the measurement space 135.

The housing 130 is provided in the upper surface thereof with a seating recess 132, a rotation preventing recess 133, and a separation recess 132*a*. The separation recess 132*a* and the seating recess 132 are connected to each other, and the seating recess 132 is connected to the opening hole 131. In addition, the rotation preventing recess 133 is spaced apart from the seating recess 132. The depth of the separation recess 132a from the upper surface of the housing 130 is greater than the depth of the seating recess 132 from the upper surface of the housing. Although not shown in the figures, the housing 130 is provided on the edge of the upper surface thereof with a stepped protrusion extending in a circumferential direction.

In the figures, the housing 130 is shown as having a cylindrical shape; however, the shape of the housing 130 may be changed depending on design of the radiation dose distribution measurement apparatus 100. In addition, the housing 130 is configured such that no light is introduced into the measurement space 135. For example, the housing 130 may be opaque, or a light blocking layer (not shown) may be formed on the surface of the housing 130. The housing 130 may be made of a material capable of shielding radiation.

The base 120 is coupled to the housing 130, and a camera 110 is disposed at the base 120. The camera 110 may be located in the measurement space 135 as a result of coupling between the base 120 and the housing 130. A fixing means 121 configured to wrap the camera 110 is disposed in the housing 130 such that the base 120 and the housing 130 are coupled to each other in place. When the base 120 and the housing 130 are coupled to each other, the housing 130 is consistently coupled to the camera 110 under guidance of the fixing means 121. The fixing means 121 may be variously changed depending on design of the radiation dose distribution measurement apparatus 100.

A lens of the camera 110 faces the center of the opening hole 131 in the measurement space 135. The camera may be a charge-coupled device (CCD) camera. Here, the construction of the CCD camera is well known, and therefore a detailed description thereof will be omitted.

The fluorescent member 140 is flat while having a predetermined thickness, and is seated in the seating recess 132 of the housing 130. The upper surface of the fluorescent member 140 does not protrude from the upper surface of the housing 130. The middle part of the fluorescent member 140 is located at the opening hole 131, and the edge part of the fluorescent member is supported by the bottom of the seating recess 132. The fluorescent member 140 is provided in the center thereof with a fluorescent through-hole 141, through which the front end of the brachytherapy insertion tool 1 that is inserted into the measurement space 135 is inserted. The fluorescent through-hole 141 is connected to the measurement space 135 via the opening hole 131. The front end of the brachytherapy insertion tool 1 may be inserted into the measurement space 135 via the fluorescent through-hole 141 and the opening hole 131. At this time, the brachytherapy insertion tool 1 is inserted through the fluorescent through-hole 141 in a state of being perpendicular to the flat surface of the fluorescent member 140. The fluorescent member 140 may emit light in response to radiation discharged from the radiation source of the brachytherapy insertion tool 1. The light may be visible light, and brightness of light that is emitted varies depending on the distribution of the radiation. The camera 110 may capture an image of light that is emitted. Since the housing 130 blocks external light so as not to be introduced into the measurement space 135, the camera may more accurately capture an image of light that is emitted, whereby it is possible to more accurately measure the distribution of radiation dose.

Here, the relationship between the fluorescent member 140 and radiation is well known, and therefore a detailed description thereof will be omitted.

Meanwhile, a portion of the fluorescent member 140 overlaps about half of the separation recess 132a. A space is defined between a portion of the fluorescent member 140 and a portion of the bottom of the separation recess 132a. A finger is put in the space through the portion of the separation recess 132a that does not overlap the fluorescent member 140 to lift the fluorescent member 140 such that the fluorescent member 140 is separated from the seating recess 132.

The cover 150 includes a cover body 151 and a guide block 152. The cover 150 blocks external light so as not to be introduced into the measurement space 135, in the same manner as the housing 130. The cover 150 may be opaque, or a light blocking layer (not shown) may be formed on the surface of the cover.

The cover body 141 is disposed on the upper surface of the housing 130, and is provided on the edge of the lower surface thereof with a catching protrusion (not shown) extending in a circumferential direction, the catching protrusion being configured to be coupled to the stepped protrusion of the housing 130. Movement of the cover body 151 in a direction perpendicular to a longitudinal direction of the housing 130 is prevented as a result of coupling between the stepped protrusion and the catching protrusion. The lower surface of the cover body 151 abuts the fluorescent member 140 in the state in which the cover body is coupled to the housing 130, whereby the fluorescent member 140 is in tight contact with the seating recess 132.

The cover body 151 is provided in the center thereof with a cover through-hole 151b, which is connected to the fluorescent through-hole 141. A pin hole 151c, which is connected to the rotation preventing recess 133, is vertically formed through the portion of the cover body 151 that is aligned with the rotation preventing recess 133.

In order to couple the cover body 151 and the housing 130 to each other, a coupling pin 160 is inserted in the state in which the rotation preventing recess 133 and the pin hole 151c are aligned with each other. The lower end of the coupling pin 160 is inserted through the pin hole 151c and is located in the rotation preventing recess 133. The cover body 151 is fixed by the coupling pin 160 located in the pin hole 151c and the rotation preventing recess 133, whereby rotation of the cover body in a circumferential direction of the housing 130 is prevented.

The guide block 152 is formed on the upper surface of the cover body 151, and is provided with a guide recess 152a extending in a longitudinal direction. The guide recess 152a is connected to the cover through-hole 151b.

Here, the brachytherapy insertion tool 1 is bent at a predetermined point thereof, and the front end (a second portion 22, see FIG. 1) of the brachytherapy insertion tool on the basis of the bent portion thereof is located in the measurement space 135 via the fluorescent and cover through-holes 141 and 151b. At this time, the front end of the brachytherapy insertion tool 1 is aligned with the vertical center 130c of each of the fluorescent and cover through-holes 141 and 151b. The rear end (a first portion 21, see FIG. 1) of the brachytherapy insertion tool 1 is inclined from the vertical center by a predetermined angle 1d. The first portion 21 of the brachytherapy insertion tool 1 is located in the guide recess 152a, and the circumference of the rear end abuts the inner surface of the guide recess 152a. Since the circumference of the rear end abuts the inner surface of the guide recess 152a, movement of the brachytherapy insertion tool 1 is prevented in a state of being mounted in the radiation dose distribution measurement apparatus 100. In addition, the brachytherapy insertion tool 1 may always be located at the same position when being mounted in the radiation dose distribution measurement apparatus 100. Consequently, it is possible to prevent the occurrence of an error due to mounting when the distribution of radiation dose is measured.

Next, operation of the radiation dose distribution measurement apparatus described above will be described with further reference to FIG. 8.

A method of measuring the distribution of radiation dose from a brachytherapy insertion tool according to the present embodiment includes a step (S10) of disposing a fluorescent member at a housing having a camera installed therein, a step (S20) of coupling a cover to the housing, a step (S30) of inserting the front end of a brachytherapy insertion tool into the housing, a step (S40) of applying, by the brachytherapy insertion tool, radiation into the housing, and a step (S50) of capturing, by the camera, an image of the interior of the housing.

A base 120 is coupled to the housing 130, and the camera 110 is disposed at the base 120. The housing 130 and the base 120 are coupled to each other in the state in which a fixing means 121 is installed in the housing 130. The camera 110 is located in a measurement space 135 as a result of coupling between the base 120 and the housing 130, and the housing 130 and the camera 110 are consistently coupled to each other by the fixing means 121. Consequently, the center of a lens of the camera 110 and the vertical center of an opening hole 131 of the housing 130 are aligned with each other.

After the housing 130 and the base 120 are coupled to each other, the fluorescent member 140 is disposed on the upper surface of the housing 130 (S10). At this time, the edge of the fluorescent member 140 is located in a seating recess 132. The fluorescent member 140 is spaced apart from the camera 110 while facing the lens of the camera such that the center of a fluorescent through-hole 141 and the center of the lens of the camera 110 are aligned with each other.

In the above description, the fluorescent member 140 is disposed at the housing 130 after the base 120 and the housing 130 are coupled to each other. Alternatively, the base 120 and the housing 130 may be coupled to each other after the fluorescent member 140 is disposed at the housing 130.

When coupling the housing 130 and the cover 150 to each other, the housing 130 and the cover 150 are coupled to each other in the state in which a stepped protrusion of the housing 130 and a catching protrusion of the cover 150 are coupled to each other (S20). Subsequently, a pin hole 151c and a rotation preventing recess 133 are aligned with each other, and then a coupling pin 160 is inserted into the rotation preventing recess 133 via the pin hole 151c. The lower end of the coupling pin 160 is located in the rotation preventing recess 133 via the pin hole 151c.

Movement of the cover 150 in directions X and Y perpendicular to a longitudinal direction Z of the housing 130 is prevented as a result of coupling between the stepped protrusion of the housing 130 and the catching protrusion of the cover 150, and rotation of the cover 150 in a circumferential direction R of the housing 130 is prevented by the coupling pin 160. As a result, the cover 150 is fixed at a predetermined position, whereby movement of the cover is prevented.

The front end of the brachytherapy insertion tool is inserted into the measurement space 135 via through-holes 141 and 151b (S30). A second portion 22 of the brachytherapy insertion tool 1 is located in the measurement space 135 as a result of insertion of the front end of the brachytherapy insertion tool. The rear end of the brachytherapy insertion tool 1 is located in a guide recess 152a, and the outer circumference of the rear end abuts the inner surface of the guide recess 152a. As a result, the brachytherapy insertion tool 1 is fixed to the cover 150. Since the brachytherapy insertion tool 1 is fixed to the cover 150, a second portion 22 of the brachytherapy insertion tool consistently abuts the fluorescent member 140.

After the brachytherapy insertion tool 1 is fixed to the radiation dose distribution measurement apparatus 100, a first portion 21 of the brachytherapy insertion tool is rotated. At this time, the second portion 22 is rotated together with the first portion 21 through a connection portion 23, whereby a second region 24b of the brachytherapy insertion tool faces a predetermined position (a tumor site).

After the position of the second region 24b is set, a radiation source is inserted into the brachytherapy insertion tool 1 so as to be located at the second portion 22 of the brachytherapy insertion tool (S40). At this time, the position of the radiation source may be adjusted. For example, when the radiation source is inserted into the brachytherapy insertion tool 1, the radiation source may be located at the second portion 22, which abuts the fluorescent member 140, such that the fluorescent member 140 and the radiation source are located on the same line. Alternatively, the radiation source may be further inserted so as to be located at the end of the second portion 22. However, the radiation source may be located higher than the fluorescent member 140 without being inserted through the fluorescent member 140. Consequently, it is possible to appropriately adjust the position of the radiation source.

Radiation is emitted from the radiation source inserted into the brachytherapy insertion tool 1 in all directions. In particular, a relatively large amount of radiation is applied to the measurement space 135 through the second region 24b, which has no shielding. The emitted radiation reacts with the fluorescent member 140, whereby light is generated.

Here, when the radiation source is located on the same line as the fluorescent member 140, radiation is emitted in all directions in a state of being parallel to the fluorescent member 140. Since a relatively large amount of radiation is applied through the second region 24b, the portion of the fluorescent member 140 aligned with the second region 24b is brighter than the other portions of the fluorescent member.

In the case in which the radiation source is located at the end of the second portion 22, radiation is emitted to the measurement space 135. Radiation collides with the surface of the fluorescent member 140, and the fluorescent member 140 reacts with the radiation, whereby light is generated. Since a larger amount of radiation is emitted from the second region 24b than a first region 24a, brighter light is generated in the portion of the fluorescent member 140 to which the radiation emitted from the second region 24b is applied than in other portions of the fluorescent member.

Brightness of light emitted from the fluorescent member 140 varies depending on the distribution of radiation. Consequently, the surroundings of the second region 24b may be brighter than the surroundings of the first region 24a.

When radiation is applied, the camera 110 photographs the fluorescent member 140 in the measurement space 135 to acquire an image (see FIG. 9). A controller (not shown) calculates the position at which light is bright through the acquired image to measure the direction in which the second region 24b of the brachytherapy insertion tool 1, which has no shielding, faces. That is, the controller calculates a deviated angle D of the second region 24b on the basis of 0° through the brightness of light from the acquired image.

Meanwhile, radiation is applied in the direction deviated by a predetermined angle D on the basis of 0°. The direction of the deviated angle D is determined by rotating an inner body 20 (see FIG. 1) through manipulation of a manipulator (not shown) of the brachytherapy insertion tool 1. Here, when the manipulator is rotated 30° on the basis of 0°, the second region 24b must be rotated 30° together with the manipulator. The controller determines whether the second region 24b has been rotated 30°.

That is, radiation is emitted from the second region 24b, and the portion of the fluorescent member 140 to which the radiation is applied emits light. At this time, brightness of light varies depending on the distribution of radiation, and the position that the second portion 22 faces is checked through the brightness of light.

Next, angle calculation will be described in detail.

First, when a captured image is input, center coordinates are determined. The center coordinates become a criterion for angle calculation. When the center coordinates are determined, signal intensity for each angle is extracted.

Signal intensity may be extracted using a contour line. When the contour line is used, a measured signal has a sine wave. At this time, the difference between the highest point and the lowest point of the measured signal must be great, and noise must not be mixed with the measured signal. In order to remove noise, smoothing is performed. At this time, an average is calculated to increase a signal-to-noise ratio (SNR). In addition, a parameter, such as a threshold value or order of a fitting function, may be used to easily extract the portion that has the greatest signal part from the measured signal.

When a specific signal intensity value is set and points having the same intensity as the value are connected to each other, the contour line passes through the point distant from the center in the direction in which intensity is high, and the contour line passes through the point closed to the center in the direction in which intensity is low. As a result, it is possible to obtain the graph shown in FIG. 10. There are two mountains and a valley therebetween. Here, the actual direction of radiation is the direction of the valley between the mountains. The directions of the two mountains are accurately checked, and then the middle between the two directions is found to find the actual direction of radiation. Consequently, the distance from the center to the contour line is drawn to detect the direction in which the signal is strong.

In addition, signal intensity may be extracted using a concentric circle. One concentric circle having a uniform distance from a predetermined center is specified, and signal intensity is drawn along the concentric circle to detect the direction in which the signal is strong.

Signal intensity for each angle is extracted to detect a peak. At this time, one or more peaks may be detected. That is, a peak is generated from a signal in a direction from 0° to 360°. There may be no peak or two peaks depending on signal distribution or the direction in which 0° is defined. In the case in which there is no peak, the definition of 0° is changed (phase shift) to detect a peak, and then 0° is changed so as to have the original definition.

In the case in which there are two peaks, the direction of the second region 24b is one, and the median between the two peaks may be the direction. However, the direction of the second region may be median between the two peaks or a value obtained by adding 180° thereto depending on the distance between the two peaks.

Consequently, the angle at which the peak is located may be output to measure the position at which the second region 24b is deviated (rotated) on the basis of 0°.

Meanwhile, a radiation dose distribution measurement apparatus according to another embodiment of the present invention further includes a lifting unit (not shown) while including the components according to the embodiment shown in FIGS. 1 to 10 without change.

The lifting unit includes a motor, a screw, and a nut, and is disposed at the housing 130 or the cover 150 so as to be connected to the fluorescent member 140. The screw and the nut form a pair. The nut is connected to the fluorescent member 140, and the screw is coupled to the nut. The screw is connected to the motor. When the screw is rotated by the motor, the fluorescent member 140, to which the nut is connected, may move upwards and downwards.

Meanwhile, a space (not shown) in which the fluorescent member 140 is movable is formed between the housing 130, at which the fluorescent member 140 is located, and the cover 150. The fluorescent member 140 may move in a direction toward the camera 110 or a direction distant from the camera 110 in response to rotation of the screw. The fluorescent member 140 may be rectilinearly moved in the space by the lifting unit, whereby the position of the fluorescent member 140 may be variously changed depending on measurement conditions.

Since the position of the fluorescent member 140 is changed by the lifting unit, three-dimensional radiation dose distribution measurement is possible. As a result, the direction in which the second region 24 faces may be more accurately measured.

Many features described in connection with the embodiment shown in FIGS. 1 to 10 may be applied to the present embodiment.

Although the preferred embodiments of the present invention have been described above in detail, the scope of rights of the present invention is not limited thereto, and various modifications and improvements implemented by those skilled in the art using a basic concept of the present invention defined in the appended claims also belong to the scope of rights of the present invention.

The invention claimed is:

1. An apparatus for measuring a distribution of radiation dose from a brachytherapy radiation source, the apparatus being configured to measure the distribution of radiation dose emitted from a brachytherapy insertion tool, the apparatus comprising:
   a housing having defined therein a measurement space in which the brachytherapy insertion tool is located;
   a fluorescent member disposed at the housing, the fluorescent member being configured to react with radiation emitted to the measurement space and to emit light;
   a camera disposed in the housing; and
   a cover coupled to one surface of the housing, the cover being configured to cover the fluorescent member, wherein
   radiation emitted from a brachytherapy radiation source transferred to the brachytherapy insertion tool is applied to the fluorescent member in the measurement space to emit light, and
   an image of the light is captured by the camera,
   wherein the fluorescent member is flat, is disposed perpendicular to the brachytherapy insertion tool guided to the measurement space, and is provided with a fluorescent through-hole, through which the brachytherapy insertion tool is inserted so as to be installed.

2. The apparatus according to claim 1, wherein the cover comprises a cover body having a cover through-hole, through which the brachytherapy insertion tool is inserted, formed therein.

3. The apparatus according to claim 2, wherein the cover further comprises an insertion tool guide formed at the cover body, the insertion tool guide being provided with a guide recess configured to guide the brachytherapy insertion tool to the cover through-hole.

4. The apparatus according to claim 1, further comprising a coupling pin inserted into the housing through the cover, the coupling pin being configured to prevent movement of the cover.

5. The apparatus according to claim 1, wherein the housing blocks external light so as not to be introduced into the measurement space when the brachytherapy insertion tool is mounted to the cover.

6. The apparatus according to claim 1, wherein the camera is disposed at one side of the measurement space, and a center of a lens of the camera is located on an identical line to a center of the brachytherapy insertion tool inserted into the measurement space.

7. An apparatus for measuring a distribution of radiation dose from a brachytherapy radiation source, the apparatus being configured to measure the distribution of radiation dose emitted from a brachytherapy insertion tool, the apparatus comprising:
a housing having defined therein a measurement space in which the brachytherapy insertion tool is located;
a fluorescent member disposed at the housing, the fluorescent member being configured to react with radiation emitted to the measurement space and to emit light;
a camera disposed in the housing; and
a cover coupled to one surface of the housing, the cover being configured to cover the fluorescent member, wherein
radiation emitted from a brachytherapy radiation source transferred to the brachytherapy insertion tool is applied to the fluorescent member in the measurement space to emit light,
an image of the light is captured by the camera, and a lifting unit disposed at the housing, the lifting unit being configured to set a position of the fluorescent member.

8. A method of measuring a distribution of radiation dose from a brachytherapy radiation source, the method comprising:
disposing a fluorescent member at a housing having a camera disposed therein;
coupling the housing and a cover to each other in a state in which the fluorescent member is interposed therebetween;
inserting a front end of a brachytherapy insertion tool into a measurement space of the housing;
transferring a brachytherapy radiation source into the brachytherapy insertion tool; and
capturing an image of the measurement space to which radiation is applied and analyzing the captured image, wherein
a portion of the fluorescent member to which radiation from the brachytherapy radiation source is applied reacts with the radiation and generates light, brightness of the light varies depending on distribution of the radiation, and a position at which the light is bright is calculated to measure a direction in which the brachytherapy insertion tool has no shielding.

* * * * *